(12) United States Patent
Hancock et al.

(10) Patent No.: US 10,610,284 B2
(45) Date of Patent: Apr. 7, 2020

(54) ELECTRICAL CONNECTOR FOR AN ELECTROSURGICAL APPARATUS

(71) Applicant: CREO MEDICAL LIMITED, Chepstow, Monmouthshire (GB)

(72) Inventors: Christopher Paul Hancock, Bath (GB); Francis Amoah, Chepstow (GB); Julian Mark Ebbutt, Ross-on-Wye (GB); Jeremy Paul Gardner, Windsor (GB); Robin Alexander Crossley, Windsor (GB); Rohan Monico, Cardiff (GB)

(73) Assignee: CREA MEDICAL LIMITED, Chepstow (GB)

( * ) Notice: Subject to any disclaimer, the term of this patent is extended or adjusted under 35 U.S.C. 154(b) by 402 days.

(21) Appl. No.: 15/327,569

(22) PCT Filed: Jul. 20, 2015

(86) PCT No.: PCT/GB2015/052099
§ 371 (c)(1),
(2) Date: Jan. 19, 2017

(87) PCT Pub. No.: WO2016/012773
PCT Pub. Date: Jan. 28, 2016

(65) Prior Publication Data
US 2017/0143404 A1 May 25, 2017

(30) Foreign Application Priority Data
Jul. 21, 2014 (GB) .................................. 1412910.0

(51) Int. Cl.
*A61B 18/12* (2006.01)
*A61B 46/10* (2016.01)
*A61B 18/00* (2006.01)

(52) U.S. Cl.
CPC .......... *A61B 18/12* (2013.01); *A61B 18/1206* (2013.01); *A61B 46/10* (2016.02); *A61B 2018/00178* (2013.01)

(58) Field of Classification Search
CPC ..... A61B 18/12; A61B 18/1206; A61B 18/14; A61B 18/1442; A61B 18/1448; A61B 2018/00178; A61B 46/10
See application file for complete search history.

(56) References Cited

U.S. PATENT DOCUMENTS

| 4,914,521 A | 4/1990 | Adair |
|---|---|---|
| 5,496,259 A | 3/1996 | Perkins |

(Continued)

FOREIGN PATENT DOCUMENTS

| CN | 104518351 A | 4/2015 |
|---|---|---|
| DE | 298 14 892 U1 | 1/1999 |

(Continued)

OTHER PUBLICATIONS

British Search Report of related British Patent Application No. 1412910.0 dated May 14, 2015.

(Continued)

*Primary Examiner* — Michael F Peffley
*Assistant Examiner* — Khadijeh A Vahdat
(74) *Attorney, Agent, or Firm* — Arent Fox LLP

(57) ABSTRACT

An electrosurgical apparatus comprising an electrosurgical instrument for delivering RF energy and/or microwave frequency energy into biological tissue, an interference cable for conveying radiofrequency (RF) and/or microwave frequency energy between an electrosurgical generator and the electrosurgical instrument, wherein a sterile barrier sheath surrounds a connection interface between the instru- (Continued)

ment and interface cable. The sterile barrier sheath and instrument may be a sterilisable unit suitable for repeated use.

15 Claims, 9 Drawing Sheets

(56) References Cited

U.S. PATENT DOCUMENTS

| | | | |
|---|---|---|---|
| 5,498,230 | A | 3/1996 | Adair |
| 5,540,683 | A | 7/1996 | Ichikawa et al. |
| 5,803,905 | A | 9/1998 | Allred et al. |
| 5,873,814 | A | 2/1999 | Adair |
| 5,876,328 | A | 3/1999 | Fox et al. |
| 6,338,657 | B1 | 1/2002 | Harper et al. |
| 2001/0025173 | A1 | 9/2001 | Ritchie et al. |
| 2001/0056221 | A1 | 12/2001 | Verschuur |
| 2002/0010463 | A1 | 1/2002 | Mulier et al. |
| 2005/0113815 | A1 | 5/2005 | Ritchie et al. |
| 2006/0161137 | A1* | 7/2006 | Orban, III ............ A61B 34/71 606/1 |

FOREIGN PATENT DOCUMENTS

| | | |
|---|---|---|
| EP | 1 862 133 A1 | 12/2007 |
| EP | 1 997 452 A2 | 12/2008 |
| EP | 2 329 783 A1 | 6/2011 |
| EP | 2 854 236 A1 | 4/2015 |
| GB | 2483154 A | 2/2012 |
| GB | 2487288 A | 7/2012 |
| WO | WO 96/17558 A1 | 6/1996 |
| WO | WO 2008/059248 A1 | 5/2008 |
| WO | WO 2015/042898 A1 | 4/2015 |

OTHER PUBLICATIONS

Combined British Search and Examination Report of related British Patent Application No. 1512712.9 dated Jan. 21, 2016.
Search Report issued in corresponding Singapore Application No. 11201700405R dated Mar. 1, 2018.
Wriiten Opinion issued in corresponding Singapore Application No. 11201700405R dated Apr. 2, 2018.
International Search Report and Written Opinion of related International Patent Application No. PCT/GB2015/052099 dated Oct. 1, 2015.
Chinese Search Report of related Chinese Patent Application No. 201580042903.9 dated Oct. 16, 2018.

* cited by examiner

SECTION A-A

SCALE 2:1

ELECTRICAL CONNECTOR FOR AN ELECTROSURGICAL APPARATUS

CROSS-REFERENCE TO RELATED APPLICATIONS

This application is a National Stage entry of International Application No. PCT/GB2015/052099, filed Jul. 20, 2015, which claims priority to British Patent Application No. 1412910.0, filed Jul. 21, 2014. The disclosures of the priority applications are incorporated in their entirety herein by reference.

FIELD OF THE INVENTION

The invention relates to an electrosurgical apparatus and device for delivering radiofrequency and/or microwave frequency energy into biological tissue. In particular, the invention relates to an electrosurgical instrument capable of delivering radiofrequency (RF) energy for cutting tissue and/or microwave frequency energy for haemostasis (i.e. sealing broken blood vessels by promoting blood coagulation).

BACKGROUND TO THE INVENTION

Surgical resection is a means of removing sections of organs from within the human or animal body. Such organs may be highly vascular. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood free cutting. For endoscopic procedures, it is also undesirable for a bleed to occur and not to be dealt with as soon or as quickly as possible, or in an expedient manner, since the blood flow may obscure the operator's vision, which may lead to the procedure needing to be terminated and another method used instead, e.g. open surgery.

Electrosurgical generators are pervasive throughout hospital operating theatres, for use in open and laparoscopic procedures, and are also increasingly present in endoscopy suites. In endoscopic procedures, the electrosurgical accessory is typically inserted through a lumen inside an endoscope, known as the instrument channel. Considered against the equivalent access channel for laparoscopic surgery, such a lumen is comparatively narrow in bore and greater in length. In the case of a bariatric patient the surgical accessory may have a length of 300 mm from handle to RF tip, whereas the equivalent distance in a laparoscopic case can be in excess of 2500 mm.

Instead of a sharp blade, it is known to use radiofrequency (RF) energy to cut biological tissue. The method of cutting using RF energy in based on the principle that as an electric current passes through a tissue matrix (aided by the ionic contents of the cells and the intercellular electrolytes), the impedance to the flow of electrons across the tissue generates heat. When an RF voltage is applied to the tissue matrix, enough heat is generated within the cells to vaporise the water content of the tissue. As a result of this increasing desiccation, particularly adjacent to the RF emitting region of the instrument (referred to herein as an RF blade) which has the highest current density of the entire current path through tissue, the tissue adjacent to the cut pole of the RF blade loses direct contact with the blade. The applied voltage is then appears almost entirely across this void which ionises as a result, forming a plasma, which has a very high volume resistivity compared to tissue. This differentiation is important as it focusses the applied energy to the plasma that completed the electrical circuit between the cut pole of the RF blade and the tissue. Any volatile material entering the plasma slowly enough is vaporised and the perception is therefore of a tissue dissecting plasma.

Patient safety is a critical factor for any electrosurgical device. There are two primary concerns: that the patient (and operators) should not be exposed to unsafe electrical signals (i.e. voltages or currents) and that the electrosurgical apparatus or device should not be a source of infection (i.e. the patient facing part of the apparatus should be sterile (and sterilisable if repeated use is intended).

SUMMARY OF THE INVENTION

At its most general, the present invention provides a sterile barrier sheath (or sleeve) that covers an interface cable between an electrosurgical instrument and a generator in order to exclude the interface cable from a sterile zone and hence obviate sterilisation of the interface cable. The sterile barrier sheath may be secured to and sterilisable with the electrosurgical instrument.

Thus, in one aspect the present invention provides an electrosurgical apparatus comprising: an electrosurgical instrument for delivering RF energy and/or microwave frequency energy into biological tissue; and an interface cable for conveying radiofrequency (RF) and/or microwave frequency energy between an electrosurgical generator and the electrosurgical instrument, wherein the electrosurgical instrument comprises: a connection interface that is cooperable with a terminal connector of the interface cable, and a sterile barrier sheath surrounding the connection interface, the sterile barrier sheath being extendable over a portion of the interface cable to surround a connection between the connection interface and terminal connector.

This aspect of the invention can also provide an electrosurgical instrument for delivering RF energy and/or microwave frequency energy into biological tissue, the electrosurgical instrument comprising: a connection interface that is cooperable with a terminal connector of an interface cable for conveying radiofrequency (RF) and/or microwave frequency energy between an electrosurgical generator and the electrosurgical instrument, and a sterile barrier sheath mounted around the connection interface, the sterile barrier sheath being extendable away from the connection interface to surround a connection between the connection interface and the interface cable.

In this arrangement, the sterilization burden is reduced because the electrosurgical instrument is provided with a sterile barrier, e.g. a flexible sheath or cover, that can isolate the interface cable in use. Further optional features are set out below.

The sterile sheath may have a first end secured to the electrosurgical instrument, e.g. permanently via adhesive or detachably via a suitable mechanical engagement, e.g. push fit or the like.

The sterile barrier sheath may be movable from a compressed configuration, in which it defines an access opening for the connection interface, to an extended configuration, in which it extends to cover a length of the interface cable. The sterile barrier sheath may comprise a length of tubing that is concertina folded when in the compressed configuration.

The sterile barrier sheath may have a second end opposite to the first end, whereby the second end is movable relative to the first end to transfer the sterile barrier sheath between the compressed configuration and the extended configuration, e.g. by gripping and pulling on a suitable tab secured to the second end thereof.

The second end may be securable to the electrosurgical generator. The sheath may include an elastic portion which is resiliently stretchable so that the second end can reach the generator.

The sterile barrier sheath may be made from material that make it sterilisable, e.g. at the same time as the electrosurgical instrument.

The aspect discussed above may be combined where appropriate with any one or more features that are described below.

A first such feature is an electrically insulating housing for a connector on an interface cable which conveys radiofrequency (RF) and/or microwave frequency energy. The housing may be formed on the connector by an injection overmoulding process, or may be formed alone and mounted on the connector in a manufacturing step, or just prior to treatment (i.e. as a step in a surgical procedure). The interface cable may provide a connection between an electrosurgical generator which produces the RF and/or microwave frequency energy and an electrosurgical instrument or accessory for delivering the RF and/or microwave frequency energy into biological tissue. The electrosurgical instrument may form part of the sterile environment for surgery, so the electrically insulating housing may be configured to facilitate a sterilisation process, e.g. involving immersion cleaning and/or autoclaving. The material used for the electrically insulating housing may be silicone rubber.

The above idea may be expressed as an electrically insulating housing for a connector on an interface cable which conveys radiofrequency (RF) and/or microwave frequency energy, the housing comprising: a tubular body secured around the circumference of the connector, the tubular body having a passage therethrough which is open at a first end to expose a terminal end of the connector and through which the interface cable extends. The housing can thus provide safe electrical isolation between the connector and the operator.

The tubular body may be overmoulded on the connector, i.e. in situ on the interface cable. Alternatively, the tubular body may be mountable, e.g. by press fit or resilient grip, on the connector by the operator before use. A dedicated applicator may be used to mounted the tubular body in place. To provide an extra level of protection, a layer of insulating material may be deposited over the outward facing conductive parts of the connector using a heat shrinking process before the tubular body is overmoulded or mounted. The layer of insulating material may be a thin covering, e.g. having a thickness of 20 µm or less, of polyimide of Parylene C. Polyimide may be preferred because it has a high breakdown strength, which may helpfully contribute to providing an electrical breakdown barrier for the device.

The tubular body may form part of a mechanical linkage between the interface cable and the electrosurgical generator and/or the electrosurgical instrument. For example, the outer surface of the tubular body may be adapt to engage a cooperating surface on the device to which it is to be connected. In a simple example, the device (generator or instrument) may have a recessed port which surrounds an electrical connection interface for mating with the connector on the interface cable. The outer surface of the tubular body may have a tapering portion at the first end to provide an interference fit within the recessed port, and thereby provide a sealed insulation boundary around the actual connection as well as securing the interface cable in place. Other types of engagement may be used.

The outer surface of the tubular body may have a outwardly flared portion at a second end thereof, opposite the first end. The outward flare permits a limited range of movement for the interface cable as it leaves the tubular body. In addition, the flared portion provides a useful hand grip for removing the housing from the device to which it is connected. The interface cable may need to be handled by a gloved operator, so it is useful to be able to obtain a good grip.

The first end of the tubular body may extend beyond the terminal end of the connector. In other words the connector may be set back inside the housing. This may permit an isolation boundary, where insulator meets conductor, to occur further away from the interface cable than the connection interface itself.

The interface cable may be used in a surgical procedure that also uses conductive fluid, e.g. saline. In order to prevent fluid ingress into the connector, the tubular body may have an inwardly projecting rib in the passage, the inwardly projecting rib being arranged to abut the connector to seal the passage. The rib may be designed as a wiper seal or the like.

The interface cable is preferably for repeated use (i.e. it is not a disposable item). Since the interface cable may need to be used in a sterile environment, it must be capable of withstanding immersion cleaning and autoclaving. The housing may act to protect the connector from damage during the sterilization process. In order to prevent the sterilization process from damaging the inner components of the connector, i.e. the part of the connector that interfaces with the cooperating element on the generator or instrument, the housing may include a deformable bung that is insertable into the first end to close the passage. The bung may plug the open end of the interface cable in a sealing manner to prevent moisture or other material from accessing the electrical contacts. The bung is preferably present during cleaning or sterilisation. There may be two bungs associated with a single interface cable, one bung for each end. The deformable bung or bungs may be attached to the interface cable (e.g. to their respective tubular body) by a lanyard element.

The deformable bung may comprise a base element and a cylindrical stopper element formed on, e.g. bonded or otherwise attached to, the base element. The cylindrical stopper element may be the main deformable part. It may be insertable into the first end and may be made of a softer material than the base element. For example, the base element may have a Shore A hardness of 90, whereas the stopper element may have a Shore A hardness of 50. Preferably the stopper element is shaped to cooperate with the internal surface of the open end of the interface cable. For example, the cylindrical stopper element may have one or more radially projecting ribs thereon. The ribs may deform when inserted into the connector (e.g. QN or QMA connector) at the end of the cable. This arrangement may minimise the amount of air trapped in the interface cable during the sterilization or disinfection process.

In the aspect of the invention discussed above, the sterile barrier sheath can be secured to the electrosurgical instrument. Alternatively or additionally, the sterile barrier sheath may be secured to or within the insulating housing described above. For example, the sterile barrier sheath may be integrally formed with the tubular housing, e.g. as an extendable sleeve that can receive the interface cable. However, the sterile barrier sheath may also be a separate bag-like receptacle, which may be a flexible elongate sleeve that is closed at one end. The sleeve may be mounted over the connection interface before the tubular body is mounted on the interface cable. Upon mounting the tubular body, the flexible bag may be stretched over the terminal end of the interface cable, e.g. to form a physical (e.g. air tight) barrier or membrane. The membrane may be broken when the connection interface mates with a cooperating port on the electrosurgical instrument. The sleeve may be a single use, sterilised item. It may be made of any suitable plastics, e.g. polypropylene or the like. The sleeve may also be used the bungs mentioned above, e.g. during transportation. The bungs are removed before the sterile sheath is fitted (and the connections made) to the instrument.

In another arrangement, the bag-like receptacle may be sized to receive the interface cable after the tubular housing is mounted or overmoulded thereon. The tubular housing may have a substantially uniform diameter (e.g. varying by less than 3 mm, e.g. between 15 mm and 18 mm) in order to facilitate this arrangement.

With the above arrangement, the sterilization burden may be reduced because the electrosurgical instrument is provided with a sterile barrier, e.g. a flexible sheath or cover, that can isolate the interface cable in use. This is particularly important when the connection to the interface cable is close to an injection port, wherein fluid is to be introduced.

In a further, less desirable alternative, the entire cable assembly may be sterilised, e.g. using gamma sterilisation, ethylene oxide (ETO), or steam.

The tubular body is preferably made of biocompatible material, such as silicone rubber or TPE.

The interface cable may comprise: a coaxial cable for conveying the RF and/or microwave frequency energy; a first terminal connector on a first end of the coaxial cable, the first terminal connector being arranged to form an electrical connection with a cooperating connection interface on the electrosurgical generator; a second terminal connector on a second end of the coaxial cable, the second terminal connector being arranged to form an electrical connection with a cooperating connection interface on the electrosurgical instrument; a first insulating housing mounted over the first terminal connector, the first insulating housing comprising a first tubular body secured around the circumference of the first terminal connector; and a second insulating housing mounted over the second terminal connector, the second insulating housing comprising a second tubular body secured around the circumference of the first terminal connector.

The first insulating housing and second insulating housing may have any of the properties discussed above. For example, the first tubular body and the second tubular body may be overmoulded on the first terminal connector and second terminal connector respectively, or moulded separately and mounted e.g. using a press fit or the like during a surgical procedure. A dedicated tool may be provided for attached and detachment of the overmoulded components. The terminal connector closer to the electrosurgical instrument may be provided with the bag-like sterilising receptacle mentioned above.

Each of the first insulating housing and second insulating housing may have a respective deformable bung that is insertable into its respective tubular body. The deformable bung(s) may be attached to the interface cable by a lanyard element. Alternatively they may be free to be disposed of after use. To prevent inadvertent contamination of the inside of the connector by its respective bung, it may be desirable to cover or cap the cylindrical stopper parts of the bungs when the interface cable is in surgical service. In a preferred arrangement, the deformable bungs for each end of the interface cable may be connectable together in a nested manner whereby the stopper part of one bung fits into a corresponding recess on the other bung. A separate storage cap may be provided for covering the remaining exposed stopper part. This arrangement has the additional advantage of being a compact storage solution.

The first terminal connector and the second terminal connector may be of different types. Preferably they are both a quick release, i.e. push fit, pull release, connectors. Such connectors are easier to manipulate and may be more conducive to use with isolation barriers as proposed herein.

In one embodiment, the first terminal connector (e.g. for connected to a port on the front panel of an electrosurgical generator) is a QN-type connector and second terminal connector (e.g. for connecting to a port on an electrosurgical instrument) is a QMA-type connector. The QMA-type connection interface can allow continuous clockwise or counter clockwise rotation of the instrument relative to the interface cable, which may improve instrument control.

In a preferred embodiment, the coaxial cable may comprise a low loss large diameter microwave cable assembly, e.g. Sucoflex® 104E or 104PE cable from Huber & Suhner. The connector used to connect the interface cable to the electrosurgical instrument is preferably a quick release connector, e.g. a QMA-type coaxial connector from Huber & Suhner. This arrangement offers a number of advantages over other standard microwave connection arrangements:

(1) the connection can be made by pushing one connector onto the other (rather than screwing) using a minimal amount of force. This ensures that a good connection is made each time as the operator can feel and hear one connector clicking into place on top of the other connector—this procedure is more difficult using conventional screw connectors, where the connector should be torqued up properly and where there is a risk of cross threading occurring;

(2) the connection is broken by pulling back a sleeve of one connector (this mechanism ensures that the connection cannot be broken accidentally during operation). This operation is also straightforward for the operator to implement, i.e. no specialised training is required; and (3) the arrangement allows the device or instrument to be mechanically rotated around the thick low loss cable with ease (this is not possible using conventional screw based connector arrangements, e.g. SMA, where there is a risk of the connection becoming broken or lost accidentally due to one connector loosening when a force is applied to the instrument handle against the large diameter cable assembly or the user tries to rotate the instrument handle whilst keeping the large diameter cable in a fixed position.

Also disclosed herein is an electrosurgical apparatus comprising: an electrosurgical instrument for delivering RF energy and/or microwave frequency energy into biological tissue; and an interface cable for conveying radiofrequency (RF) and/or microwave frequency energy between an electrosurgical generator and the electrosurgical instrument, wherein the electrosurgical instrument comprises an integral cable tail that extends away from the electrosurgical instrument and terminates at a connection interface that is cooperable with a terminal connector of the interface cable, and wherein the cable tail is arranged to have a length that extends beyond a sterile zone around the electrosurgical instrument. In this arrangement the sterilization burden on the interface cable may be reduced (e.g. it may only need to be subjected to immersion cleaning) because it lies outside the sterile region associated with the surgical procedure. The interface cable may have any of the features discussed above.

Herein, radiofrequency (RF) may mean a stable fixed frequency in the range 10 kHz to 300 MHz and microwave frequency may mean a stable fixed frequency in the range 300 MHz to 100 GHz. The RF energy should have a frequency high enough to prevent the energy from causing nerve stimulation and low enough to prevent the energy from causing tissue blanching or unnecessary thermal margin or damage to the tissue structure. Preferred spot frequencies for the RF energy include any one or more of: 100 kHz, 250 kHz, 400 kHz, 500 kHz, 1 MHz, 5 MHz. Preferred spot frequencies for the microwave energy include 915 MHz, 2.45 GHz, 5.8 GHz, 14.5 GHz, 24 GHz.

BRIEF DESCRIPTION OF THE DRAWINGS

Examples embodying the invention are discussed in detail below with reference to the accompanying drawings, in which.

DETAILED DESCRIPTION; FURTHER OPTIONS AND PREFERENCES

Figure 1:
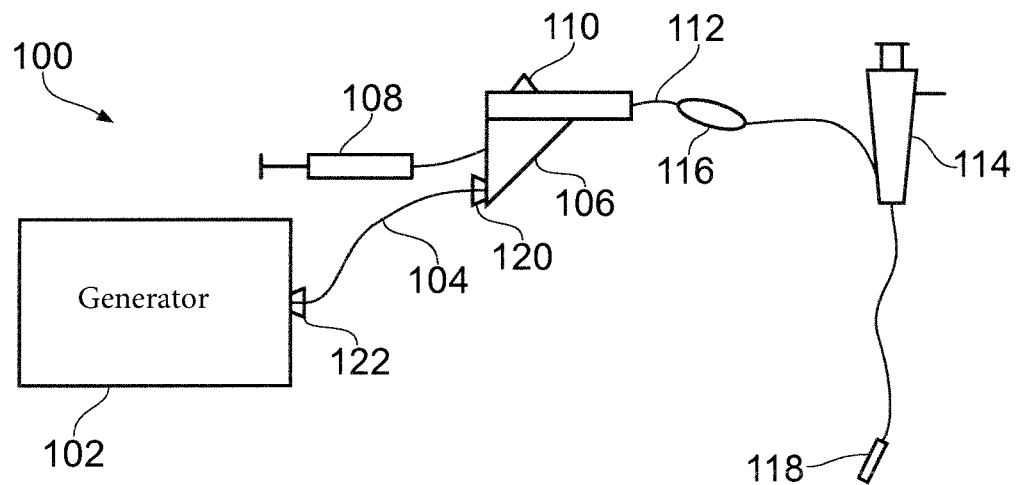
FIG. 1 is a schematic view of a complete electrosurgery system in which the present invention is applied.

FIG. 1 is a schematic diagram of a complete electrosurgery system 100 that is capable of selectively supplying to the distal end of an invasive electrosurgical instrument any or all of RF energy, microwave energy and fluid, e.g. saline or hyaluronic acid. The system 100 comprises a generator 102 for controllable supplying RF electromagnetic (EM) energy and/or microwave frequency EM energy. A suitable generator for this purpose is described in WO 2012/076844, which is incorporated herein by reference.

The generator 102 is connected to an interface joint 106 by an interface cable 104. The interface joint 106 is also connected to receive a fluid supply 107 from a fluid delivery device 108, such as a syringe. The interface joint 106 houses a needle movement mechanism that is operable by sliding a trigger 110. The function of the interface joint 106 is to combine the inputs from the generator 102, fluid delivery device 108 and needle movement mechanism into a single flexible shaft 112, which extends from the distal end of the interface joint 106. The internal configuration of the interface joint 106 is discussed in more detail below.

The flexible shaft 112 is insertable through the entire length of an instrument (working) channel of an endoscope 114. A torque transfer unit 116 is mounted on a proximal length of the shaft 112 between the interface joint 106 and endoscope 114. The torque transfer unit 116 engages the shaft to permit it to be rotated within the instrument channel of the endoscope 114.

The flexible shaft 112 has a distal assembly 118 that is shaped to pass through the instrument channel of the endoscope 114 and protrude (e.g. inside the patient) at the distal end of the endoscope's tube. The distal end assembly includes an active tip for delivering RF EM energy and/or microwave EM energy into biological tissue and a retractable hypodermic needle for delivering fluid. These combined technologies provide a unique solution for cutting and destroying unwanted tissue and the ability to seal blood vessels around the targeted area. Through use of the retractable hypodermic needle, the surgeon is able to inject saline and/or hyaluronic acid with added marker dye between tissues layers in order to distend and mark the position of a lesion to be treated. The injection of fluid in this manner lifts and separates the tissue layers making it both easier to resect around the lesion and plane through the submucosal layer, reducing the risk of bowel wall perforation and unnecessary thermal damage to the muscle layer.

In this arrangement, the interface joint 106, flexible shaft 102 and distal assembly 118 form an electrosurgical instrument. The present invention concerns the connections require to transfer RF and/or microwave frequency energy from the electrosurgical generator 102 to the electrosurgical instrument. Consequently, the invention can be applicable to any type of electrosurgical instrument or accessory that is designed to receive power from an electrosurgical generator. For example, the invention is applicable to instruments that are used in laparoscopic or open surgery as well as to instruments suitable for endoscopic use.

The interface cable 104 is a coaxial cable, e.g. a Sucoform 047 cable or a Sucoform 86 cable. The interface cable 104 connects at its distal end into the interface joint 106 using a QMA-type coaxial connector 120, which permits continuous relative rotation between the interface joint 106 and the interface cable 104. This freedom of movement gives the operator of the instrument more flexibility during use and prevents the cable from twisting.

Similarly, the interface cable 104 connects at its proximal end into the electrosurgical generator 102 using a QN-type coaxial connector 122. Although this embodiment specifies the type of connector used, the principles of the present invention are applicable to any suitable connector for a coaxial cable.

In the invention, the exposed conductive metal parts of the connectors 120, 122 are surrounding by an electrically insulating housing, e.g. made of thermoplastic elastomer (TPE) or the like. The insulating housing can be overmoulded on each connector using conventional overmoulding techniques. The primary purpose of the housing is to ensure that adequate creepage and clearance distances are maintained across connector junction, whilst also ensuring ingress of spilt injection fluid is avoided.

Figure 2:
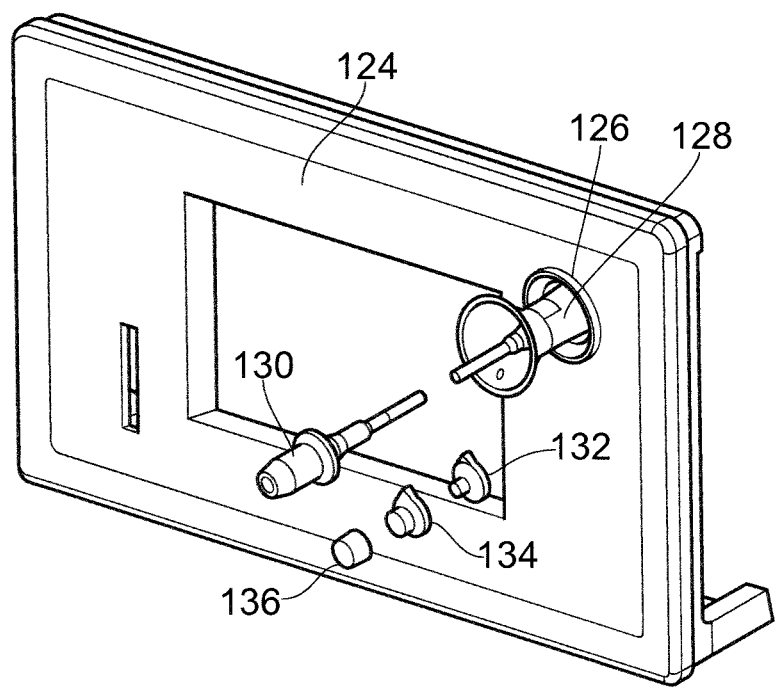
FIG. 2 is a perspective view of the components of an electrical connector housing assembly that is an embodiment of the invention, the electrical connector housing assembly being shown by a front panel of an electrosurgical generator with which the present invention may be used.

FIG. 2 shows the components of a complete connector housing system that is an embodiment of the invention. The connector housing system is shown with the front panel 124 of an electrosurgical generator. The front panel 124 includes a port 126 for receiving a QN-type connector. The QN-type connector is at the proximal end of the interface cable 104 (shown shortened here for clarity) and is surrounded by a QN-type electrical connector housing 128. The QN-type electrical connector housing 128 extends into the port 126 to provide the necessary insulation. The shape and internal configuration of the QN-type electrical connector housing 128 is discussed below with reference to FIGS. 3A to 3F.

At the distal end of the interface cable 104 there is a QMA-type connector surrounded by a QMA-type electrical connector housing 130. The QMA-type electrical connector housing 130 has a conically tapering distal end that is receivable in a connector port on an electrosurgical instrument (not shown) which is to be connected to the electrosurgical generator 102 by the interface cable. The shape and internal configuration of the QMA-type electrical connector housing 130 is discussed below with reference to FIGS. 4A to 4F.

The remaining three components of the complete connector housing system are a QMA-type sealing bung 132, a QN-type sealing bung 134 and a storage cap 136. When the interface cable 104 is disconnected from the instrument and generator, the sealing bungs 132, 134 are inserted into the respective ends of the cable, where they seal and protect the internal components. The seal is watertight in order to prevent damage from occurring during immersion cleaning.

When the interface cable 104 is connected between the generator and instrument, the sealing bungs 132, 134 are removed and stored in a stacked manner in the storage cap 136. This arrangement is discussed below with reference to FIGS. 5A and 5B.

Figure 3A:
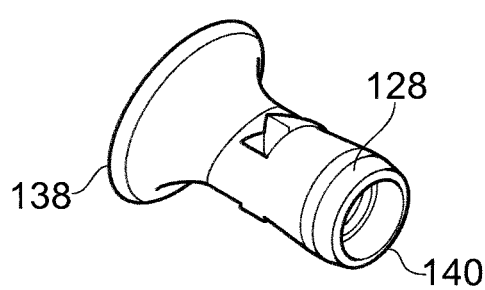
FIG. 3A is a perspective view of a QN-type electrical connector housing that is an embodiment of the invention.

A perspective view of the QN-type connector housing 128 is shown in FIG. 3A. The housing comprises a tubular body having a flared distal end 138 and a tapered proximal end 140. As shown in the side view of FIG. 3B, the flared distal end 138 terminates in a round edge that lies on an inclined plane. The middle of the tubular body is slight waisted. This shape is ergonomically designed to facilitate removal of the housing and connector from the generator by providing an easily grippable part. The housing and connector may need to be removed by an operator who is wearing gloves, so having an easily gripped part may be particularly advantageous.

The tubular body may be formed in one piece from any suitable mouldable material, such as TPE or silicone rubber. The material may have a Shore A hardness of 70 to 80.

Figure 3B:
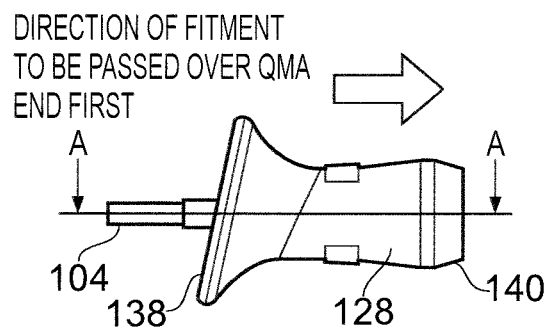
FIG. 3B is a side view of the housing shown in FIG. 3A with the QN-type electrical connector fitted inside.
Figure 3C:
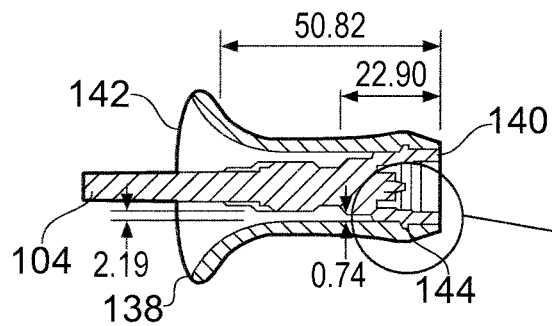
FIG. 3C is a cross-sectional view of the housing and connector shown in FIG. 3B.

FIG. 3C shows a cross-sectional view of the QN-type connector housing 128. The dimensions given are in mm. The connector housing has a internal channel 142 extending along its length from the flared distal end 138 to the tapered proximal end 140. The diameter of the internal channel 142 corresponds to the outer wall of the tubular body, i.e. it has a large diameter at the distal end that decreases to a constant value in the proximal two thirds of its length. This flaring of the distal end of the channel 142 provides some freedom for the interface cable 104 to flex.

Figure 3D:
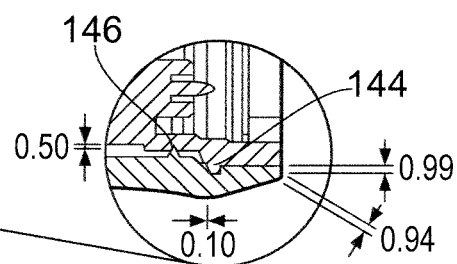
FIG. 3D is a close up view of the configuration of the inner wall of the housing shown in FIG. 3B.

Towards the proximal end of the internal channel 142 a circumferential recess 144 and a circumferential ridge 146 are provided around the inner wall of the channel. FIG. 3D shows these features more clearly. The circumferential recess 144 and the circumferential ridge 146 engage corresponding cooperating features on the QN-type connector itself in order to secure the housing in a fixed position with respect to the connector and to provide a sealing boundary to prevent fluid ingress during cleaning immersion and/or autoclave cycles. As shown in FIG. 3B, the housing in mounted over the QN-type connector by passing the housing from the opposite end (i.e. the QMA-type connector end) of the interface cable. The housing may be arranged so that it cannot slide over the QN-type connector.

Figure 3E:
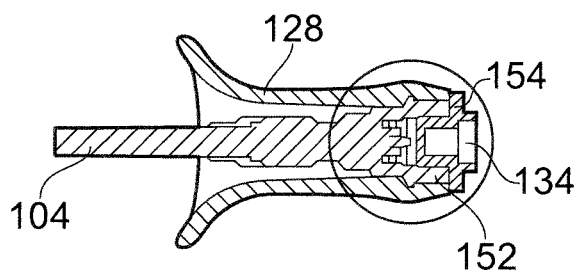
FIG. 3E is cross-sectional view the housing shown in FIG. 3A with the QN-type electrical connector fitted inside with a sealing bung closing the connector opening.

FIG. 3E shows the QN-type connector housing 128 in an unconnected state, with the sealing bung 134 inserted into the cavity 148 at the end of the QN-type connector.

Figure 3F:
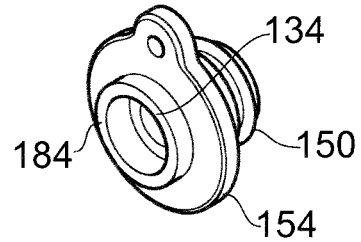
FIG. 3F is a perspective view of the sealing bung used in FIG. 3E.

As shown in FIG. 3F, the sealing bung 134 comprises an insertion portion that includes a cylindrical stopper 152 having a plurality of radially protruding ridges 150 arranged outer its outer circumference. The insertion portion terminates at a radial flange 154 which abuts the axial end of the connector when the insertion portion is mounted in the cavity 148.

The sealing bung 134 is made from a resiliently deformable material, e.g. having a Shore A hardness of 50 to 65. For example, TPE or silicone material may be used. Upon insertion in the cavity 148, the radially protruding ridges 150 abut against the inner surface of the connector to seal the open end thereof.

The shape of the bung otherwise corresponds to the shape of the cavity in order to minimise the amount of air trapped in the cavity when it is sealed.

Figures 4A, 4B:
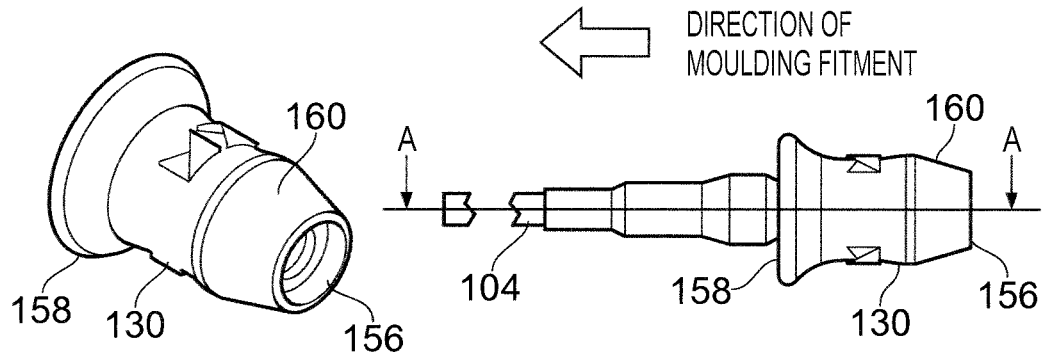
FIG. 4A is a perspective view of a QMA-type electrical connector housing that is an embodiment of the invention.
FIG. 4B is a side view of the housing shown in FIG. 4A with the QMA-type electrical connector fitted inside.

A perspective view of the QMA-type connector housing 130 is shown in FIG. 4A. The housing comprises a tubular body having a flared proximal end 158 (facing away from patient) and a distal end 156 at the end of a conically tapering section 160 that runs along the distal third of the housing 130. As shown in the side view of FIG. 4B, the flared proximal end 158 is less pronounced than for the QN-type connector housing. However, the housing is still shaped in this manner to facilitate removal of the housing and connector from the generator by providing an easily grippable part.

Similarly to the housing shown in FIG. 3A, the tubular body may be formed in one piece from any suitable mouldable material, such as TPE or silicone rubber. The material may have a Shore A hardness of 70 to 80.

Figures 4C, 4D:
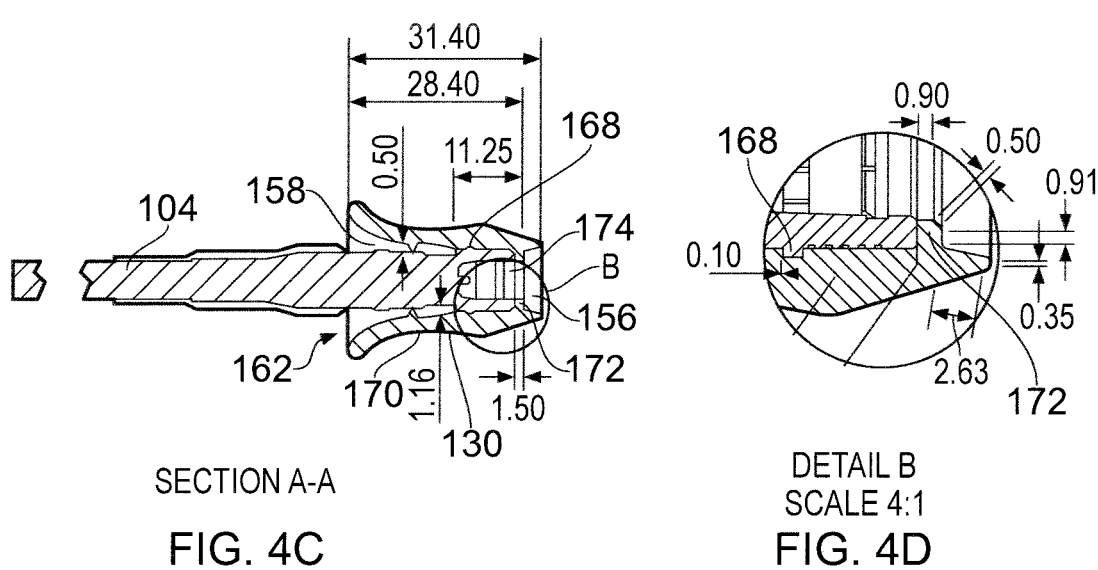
FIG. 4C is a cross-sectional view of the housing and connector shown in FIG. 4B.
FIG. 4D is a close up view of the configuration of the inner wall of the housing shown in FIG. 4B.

FIG. 4C shows a cross-sectional view of the QMA-type connector housing 130. The dimensions given are in mm. The connector housing has a internal channel 162 extending along its length from the flared proximal end 158 to the distal end 156. The diameter of the internal channel 162 corresponds to the outer wall of the tubular body, i.e. it has a large diameter at the proximal end that decreases to a constant value in the distal two thirds of its length.

Inside the internal channel 162 a circumferential recess 168 and a circumferential ridge 170 are provided around the inner wall of the channel. In addition, the proximal end of the internal channel 162 terminates at a radially inwardly projecting flange, which abuts the proximal end of the connector. FIG. 4D shows these features more clearly. The circumferential recess 168 and the circumferential ridge 170 engage corresponding cooperating features on the QMA-type connector in order to secure the housing in a fixed position with respect to the connector and to provide a sealing boundary to prevent fluid ingress during cleaning immersion and/or autoclave cycles. As shown in FIG. 4B, the housing is mounted over the QMA-type connector by passing the QMA-type connector through the internal channel 162 until the end thereof abuts the flange 172. In this embodiment, there is therefore a portion of the housing 130 that extends beyond the end of the connector. An advantage of this arrangement is that the connection between the QMA-type connector and the electrosurgical instrument is complete surround by insulating material.

Figures 4E, 4F:
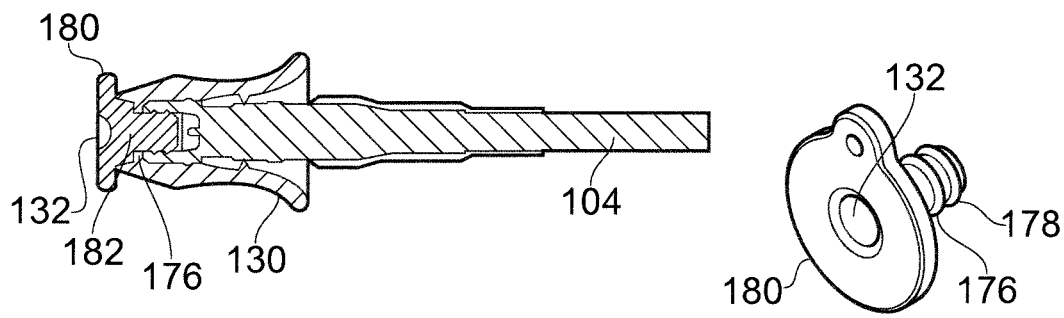
FIG. 4E is cross-sectional view the housing shown in FIG. 4A with the QMA-type electrical connector fitted inside with a sealing bung closing the connector opening.
FIG. 4F is a perspective view of the sealing bung used in FIG. 4E.

FIG. 4E shows the QMA-type connector housing 130 in an unconnected state, with the sealing bung 132 inserted into the cavity 174 at the end of the QMA-type connector.

As shown in FIG. 4F, the sealing bung 132 comprises an insertion portion that includes a cylindrical stopper 176 having a plurality of radially protruding ridges 178 arranged outer its outer circumference. The insertion portion terminates at a radial flange 180 which abuts the axial end of the housing 130. The cylindrical stopper 176 includes a base portion 182 shaped to fill the part of the internal channel that lies between the end of the connector and the end of the housing.

The sealing bung 132 may be made from the same material as the sealing bung 134 for the QN-type connection, i.e. it may be made from a resiliently deformable material, e.g. having a Shore A hardness of 50 to 65. For example, TPE or silicone material may be used. Upon insertion in the cavity 174, the radially protruding ridges 178 abut against the inner surface of the connector to seal the open end thereof.

The shape of the bung otherwise corresponds to the shape of the cavity in order to minimise the amount of air trapped in the cavity when it is sealed.

Figure 5A:
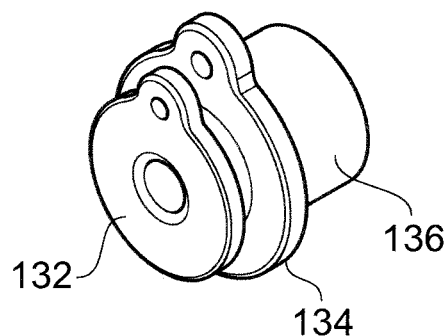
FIG. 5A is a perspective view of a storage assembly comprising the sealing bungs shown in FIGS. 3F and 4F contained in a storage cap.
Figure 5B:
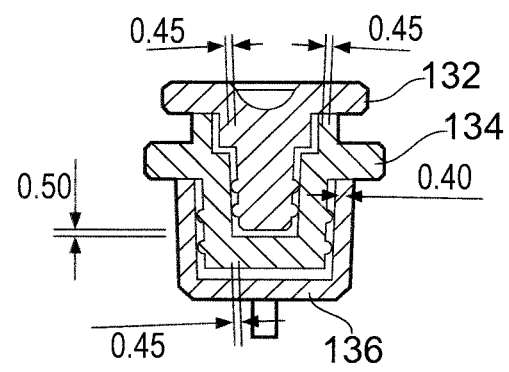
FIG. 5B is a cross-sectional view through the storage assembly of FIG. 5A.

FIGS. 5A and 5B show a storage configuration for the sealing bungs 132, 134 when the interface cable is interconnected ready for surgical use. The sealing bungs 132, 134 are able to nest together through the formation of a recess 184 (see FIG. 3F) in the sealing bung 134 for the QN-type connector which is shaped to receive the cylindrical stopper 176 of the sealing bung 132 for the QMA-type connector. To prevent the nested assembly from becoming contaminated, e.g. through contact between the cylindrical stopper 152 of the sealing bung 134 for the QN-type connector and an unsterilized surface, a storage cap 136 is mounted over the stopper 152. The storage cap 136 may be made from the same material as the sealing bungs and comprises a cup shape for forming an interference fit with the stopper 152.

Figure 6:
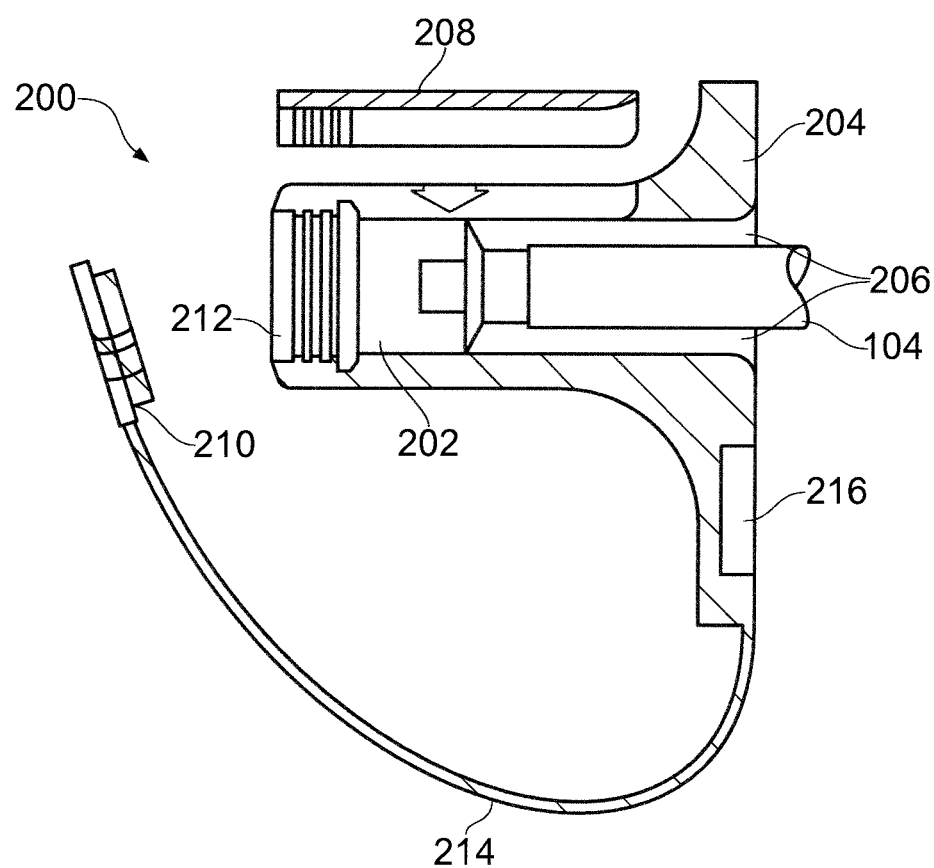
FIG. 6 is a cross-sectional view of an electrical connector housing that is another embodiment of the invention.

FIG. 6 shows another embodiment of an electrically insulating housing 200 for a connector 202 at one end of the interface cable 104. In this embodiment, the housing 200 is moulded as a rigid base 204, which defines a passage 206 for receiving the connector 202, and a snap fit lid 208 which can be pushed on to the base 204 when the connector is in the passageway to secure it in place. The snap fit lid 208 may be made of the same material as the rigid base. The drop in nature of the snap fit lid may assist in accurate location of the connector.

The housing 200 may further include a cap 210 for closing the cavity 212 in the connector, e.g. during immersion cleaning and autoclaving, similar to the sealing bungs mentioned above. The cap 210 may be permanently attached to the base 204 by a lanyard 214, e.g. formed from a thin strip of nylon. The base 204 may include a dock 216 for holding the cap when the cable is in use. The dock 216 is below the cable to prevent it from interfering with the surgical procedure.

The passage 206 may be wider then the interface cable beyond the point at which the connector is clamped. There is therefore free space 206 around the interface cable 104 in this location, which may be used for further encapsulation to increase strain relief and solid insulation.

In an adaptation of this embodiment, the rigid base 204 may be overmoulded with a softer elastomer in areas that are gripped by the user in operation.

Figure 7:
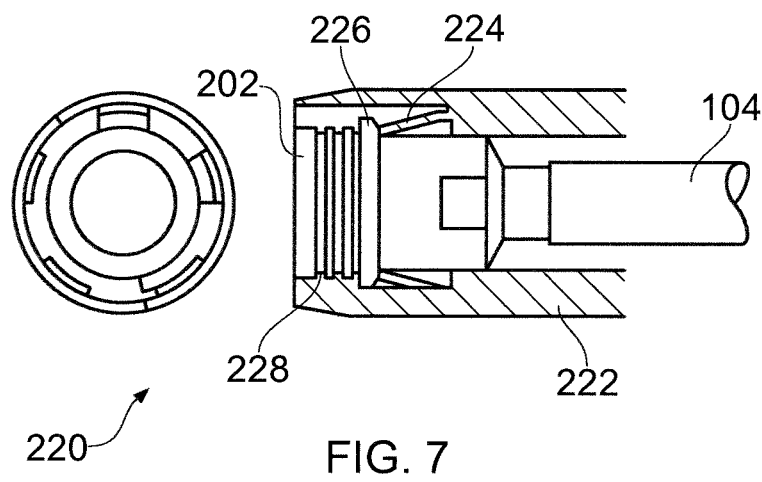
FIG. 7 is a cross-sectional view of an electrical connector housing that is another embodiment of the invention.

FIG. 7 shows another embodiment of an electrically insulating housing 220 for a connector 202 at one end of the interface cable 104. In this embodiment, the housing 220 comprises a push fit cylinder 222 which mates with the connector 202. The push fit cylinder comprises a plurality of resilient blades 224 which click into place behind a collar 226 on the connector 202 and urge the connector 202 into contact with an engagement surface 228. The engagement surface 228 is shaped to cooperate with the outer profile of the connector to form a snug fit. The housing may be made from a material that is rigid yet exhibits enough resilience for the blades 224 to operate.

Figure 8:
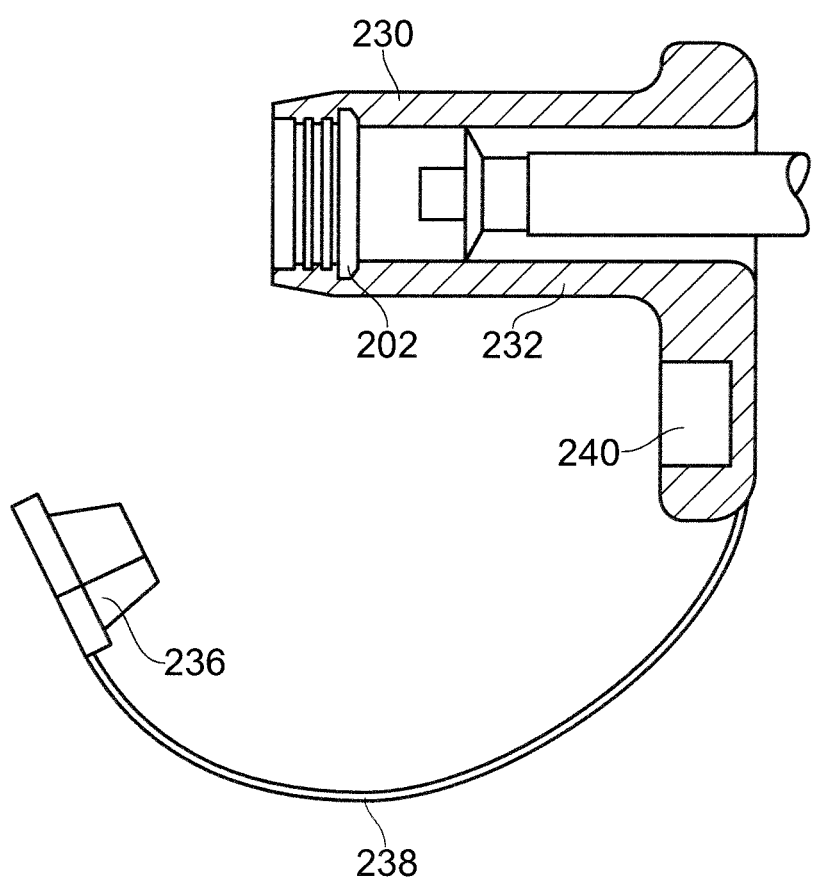
FIG. 8 is a cross-sectional view of an electrical connector housing that is another embodiment of the invention.

FIG. 8 shows another embodiment of an electrically insulating housing 230 for a connector 202 at one end of the interface cable 104. The housing 230 comprise a base 232 that is similar to the base 204 shown in FIG. 6 except that is formed from a resiliently deformable material (e.g. a soft overmoulding of a suitable silicone rubber or Pebax®). The base 232 defines a through passage 234 which has a diameter slightly small than that of the connector so that base can be pushes on to the connector and retained.

Similarly to FIG. 6, the housing includes a cap 236 that can close the cavity in the connector 202, or, when the connector is in use, can be stored in a dock 240. The cap 236 is attached to the base 230 by a lanyard 238.

Figure 9:
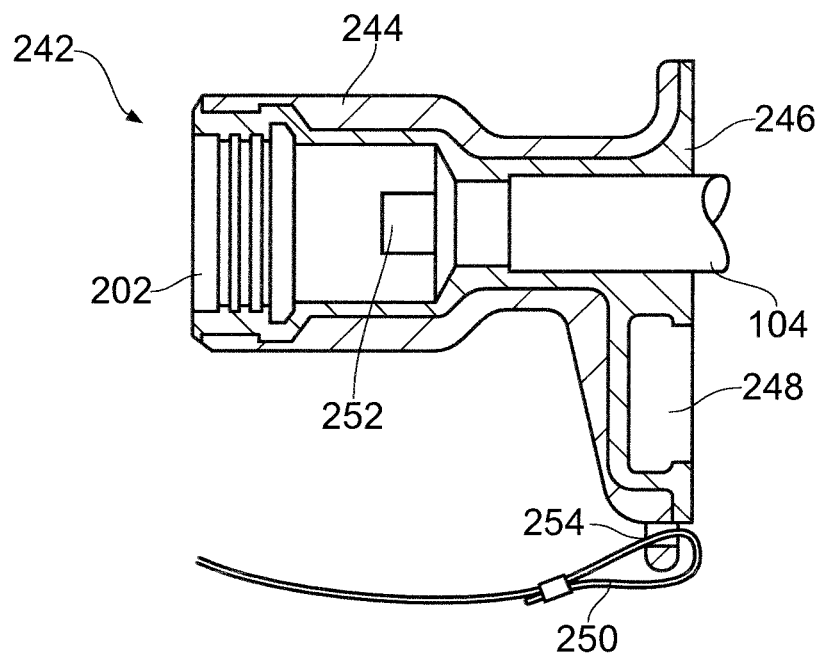
FIG. 9 is a cross-sectional view of an electrical connector housing that is another embodiment of the invention.

FIG. 9 shows another embodiment of an electrically insulating housing 242 for a connector 202 at one end of the interface cable 104. The housing 242 in this embodiment comprises two parts: a rigid inner core 246, e.g. of polypropylene, and a softer outer cover 244, e.g. having a Shore A hardness of around 80. The outer cover 244 may be made from polyvinylchloride or the like. In this embodiment, there are no gaps in the passageway through the housing 242. The inner core 246 is moulded to the connector 202 and to the end of the interface cable 104 that leads to the connector.

Similarly to the embodiments discussed with reference to FIGS. 6 and 8, the housing has a cap (not shown) for sealing the cavity at the entrance to the connector 202. A dock 248 for the cap is incorporated into the inner core. A lanyard 250 connects the cap to the outer cover 244. In this case the lanyard 250 is a wire that is looped through an anchor 254 hole formed in the outer cover 244.

The housing in this embodiment may need to be manufactured in situ on the cable and connector. To aid location of the housing, the connector 202 may be provided with flats 252 on its outer surface.

In the examples given above, the connection between the interface cable 104 and the electrosurgical instrument occurs at the instrument itself, which is within the region that must be kept sterile, insofar as it is manipulated by the operator during the surgical procedure.

Figure 10:
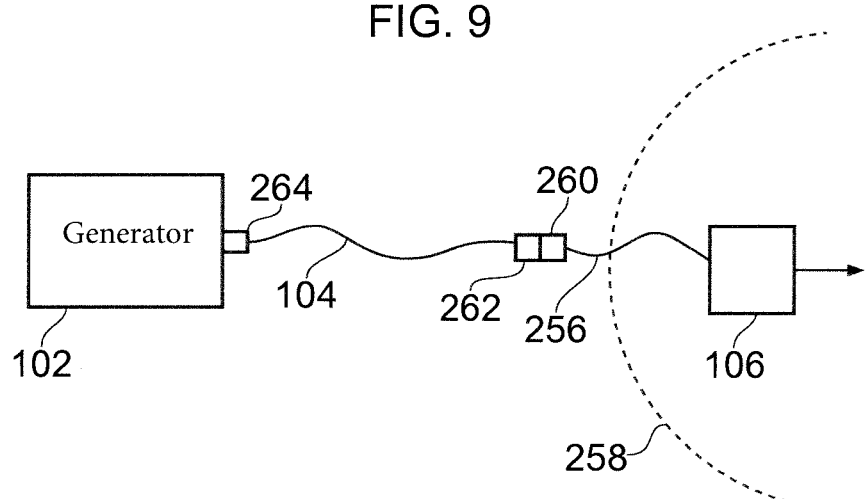
FIG. 10 is a schematic view of an interface cable interconnected between an electrosurgical generator and a sterile electrosurgical instrument in which the distal connection of the interface cable lies outside a region of required sterility.

FIG. 10 is a schematic view of an alternative configuration for interconnecting an electrosurgical generator 102 and an electrosurgical instrument 106. In this embodiment, the electrosurgical instrument 106 is provided with a cable tail 256 which extends far enough away from the instrument to lie outside the sterile environment boundary. The cable tail 256 may terminate in a connection port 260 for receiving a connector 262 at a distal end of the interface cable 104. The interface cable 104 may be connected to the electrosurgical generator 102 via a connector 264 at its proximal end as set out above.

Figure 11:
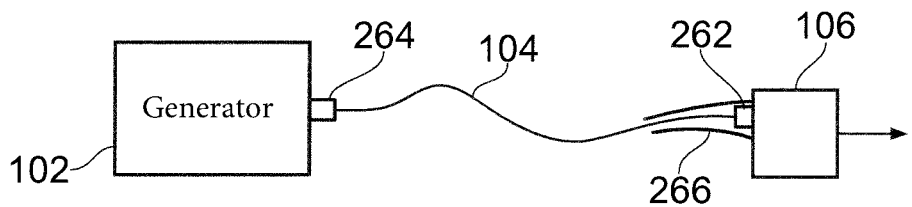
FIG. 11 is a schematic view of an interface cable interconnected between an electrosurgical generator and a sterile electrosurgical instrument in which the sterile electrosurgical instrument includes a extendable sheath.

FIG. 11 shows a schematic view of another alternative configuration for interconnecting an electrosurgical generator 102 and an electrosurgical instrument 106. In this arrangement the instrument 106 is provided with an extendable sheath 266 that can be pushed over the connector 262 at the distal end of the interface cable 104. The sheath may be a flexible tube that can be rolled or otherwise pulled over a distal length of the interface cable 104.

An advantage of the arrangements shown in FIGS. 10 and 11 is that the sterilization regime for the interface cable 104 and its connectors may be less aggressive than for the arrangements discussed above. In particular, the need for autoclaving may be avoided. This arrangement may prolong the working life of the interface cable 104.

Figure 12:
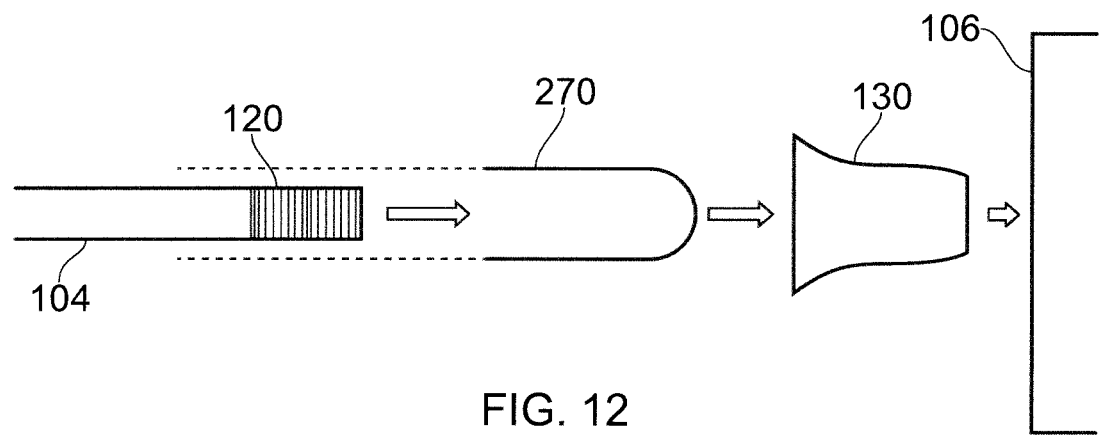
FIG. 12 is a schematic view of the terminal end of an interface cable which is inserted into a flexible bag-like receptacle to create a sterile barrier before the electrical connector housing is mounted thereon.

FIG. 12 is a schematic view of yet another sterilisation arrangement for the interface cable 104 and electric connector housing 130 that is an embodiment of the invention. Here the electrical connector housing 130 (e.g. a QMA-type connector housing as discussed above) is arranged to be mounted by press fit on to the terminal end of the interface cable 104. Before this is done, however, the terminal end of the interface cable 104 is placed inside a sterile elongate sleeve 270, i.e. a tubular bag-like receptacle. The interface cable 104 is inserted into the sleeve 270 until the connector 120 is spaced a short distance from the end of the sleeve 270. The sleeve is then folded over the end of the connector 120 and the connector housing 130 is mounted over it. As the connector housing 130 is mounted, the sleeve is pushed tightly over the cable to form a sealed membrane at the distal end of the connector 120. The interface cable is therefore sealed within a sterile environment. In use, the connector 120 is inserted into a cooperating port on the electrosurgical instrument 106. The cooperating elements of the port and connector 120 (e.g. a conductive pin or the like) pierce the membrane to effect the electrical connection.

Figure 13:
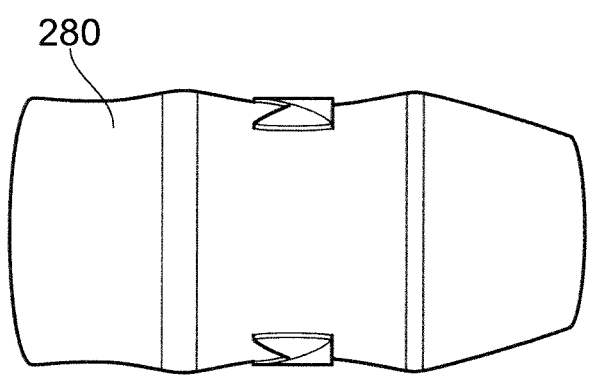
FIG. 13 is a side view of an electrical connector housing that is another embodiment of the invention.

FIG. 13 is a side view of another embodiment of a connector housing 280 that is an embodiment of the invention. The internal configuration of the connector housing 280 is the same as the embodiment discussed in FIG. 4 above and is not repeated. The external configuration is also the same except that the proximal end of the connector housing 280 does not exhibit the same external flare. Instead, the connector housing 280 has a substantially uniform external profile, where the variations in diameter of its tubular body are limited, and so that the maximum outer diameter does not exceed a predetermined threshold, e.g. 18 mm.

Figure 14:
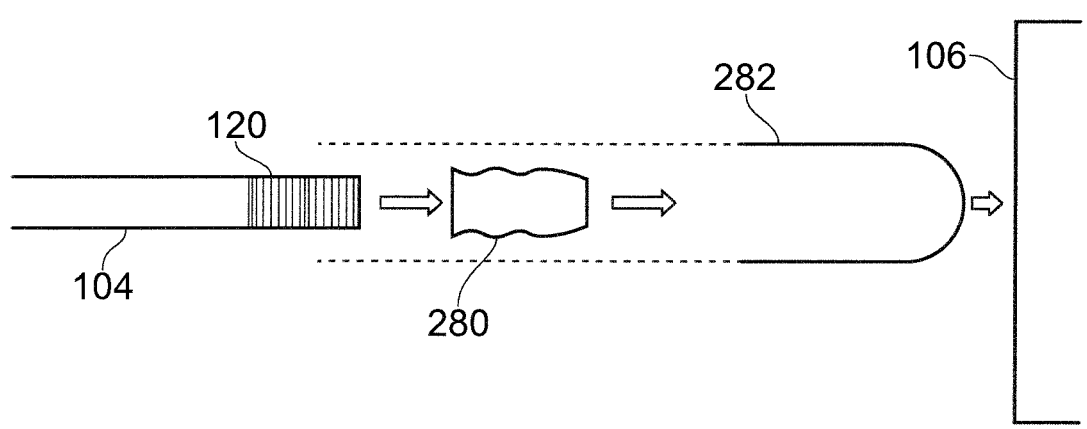
FIG. 14 is a schematic view of the terminal end of an interface cable which is inserted into a flexible bag-like receptacle to create a sterile barrier after the electrical connector housing is mounted thereon.

An advantage of controlling the outer profile of the connector housing 280 as shown in FIG. 13 is that it may facilitate use within a sterile sleeve as shown in FIG. 14. FIG. 14 is a schematic view of a sterilisation arrangement for the interface cable 104 and connector housing 280 that is an embodiment of the invention. The sterilisation arrangement is similar to that shown in FIG. 12, except that it uses a flexible sleeve 282 that has a larger diameter so that both the interface cable 104 and the connector housing 280 can be received therein. In this arrangement, the connector housing 280 is mounted (e.g. by press fit) or overmoulded on the connector 120 in a first step, following which the interface cable 104 is inserted into the sleeve 282. As in the arrangement shown in FIG. 12, the interface cable 104 is inserted until its distal end is a short distance from the end of the sleeve. The excess length of the sleeve is folded over to form a sterile membrane at the entrance to the internal channel of the connector housing 280. The folded over length of sleeve may be secured to the cable or connector housing using an appropriate fastener. An advantage of this arrangement is that the connector housing may not need to be sterilised.

Figure 15:
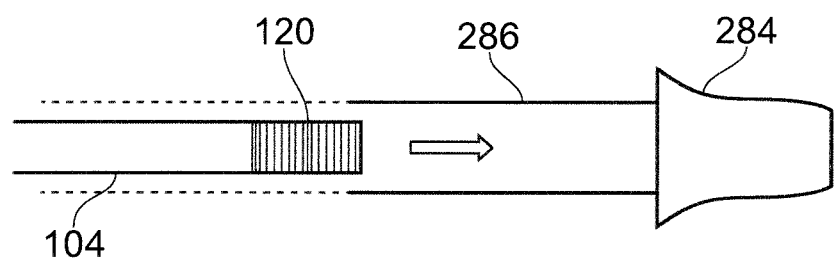
FIG. 15 is a schematic view of the terminal end of an interface cable which is inserted into a flexible bag-like receptacle that is formed integrally with the electrical connector housing to create a sterile barrier.

FIG. 15 shows another schematic view of a sterilisation arrangement for the interface cable 104 and connector housing 284 that is an embodiment of the invention. This example is similar to FIGS. 12 and 14 except that the connector housing 284 is in one piece with the sterile sleeve 286. For example, the sterile sleeve may be manufactured with the connector housing, e.g. by attaching it thereto using suitable moulding, adhesion or welding techniques. The connector housing and sleeve may thus be sterilised together and packaged as a single use item.

Figure 16A:
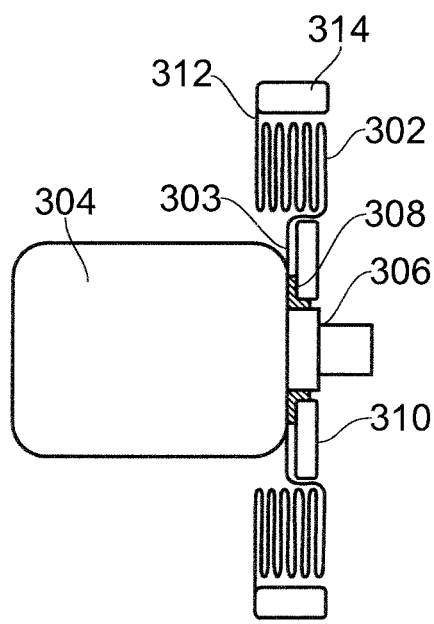
FIG. 16A is a schematic cross-sectional view of an extendable sterile sheath that is an embodiment of the invention mounted on a connection handle of an electrosurgical instrument.
Figure 16B:
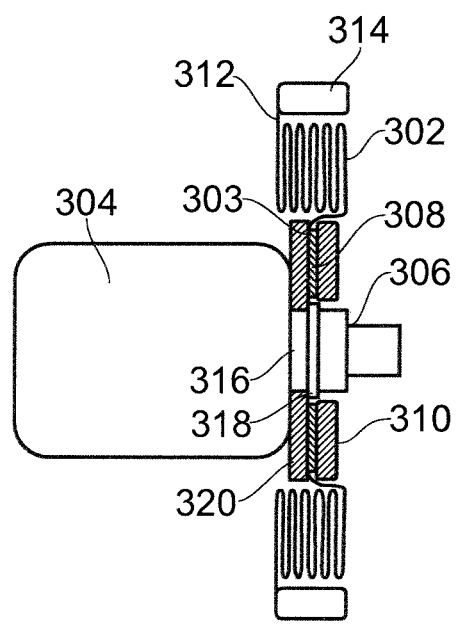
FIG. 16B is a schematic cross-sectional view of an extendable sterile sheath that is an embodiment of the invention detachably mounted on a connection handle of an electrosurgical instrument.

FIGS. 16A and 16B show further embodiments which incorporate a sterile sleeve similar to that discussed above. An advantage of these embodiment are that they obviate sterilisation of the interface cable. Instead of requiring the cable to be sterilised, the cable is assumed to be (a non-sterile) part of the generator. In such circumstances, the sterile sleeve forms a barrier between the non-sterile cable and the sterile field. Thus, in the embodiments shown in FIGS. 16A and 16B, an extendable sterile sheath is formed integrally with or mounted on an electrosurgical instrument around the connection port (e.g. on the handle) where it is connected to the electrosurgical generator. Once extended, the sterile sheath creates a tube-like cover which provides a physical barrier between a non-sterile cable and the sterile field, thereby preventing contamination from the cable.

FIG. 16A shows an embodiment in which an extendable sterile sheath 302 is permanently mounted on a handle 304 of an electrosurgical instrument. The handle 304 has a connection port 306 (e.g. a QMA connector) at a distal end thereof. The connection port 306 is arranged to electrically connect to one end of a coaxial interface cable (not shown), which may have one of the overmoulded housings discussed above formed thereon.

In this embodiment, the sterile sheath 302 comprises a length of plastic tubing having a first end 303 positioned over the connection port 306 and secured to housing 304 by adhesive 308. A rigid annular cover 310 (e.g. made from acrylonitrile butadiene styrene (ABS) is fixed over the adhesive 308 to protect the connection. The cover 310 can be fixed to the handle 304 either via mechanical interlock or through an adhesive such as a cyan acolyte.

A second end 312 of the sterile sheath is attached to a pull tab 314 which can be gripped by a user to pull the sterile sheath into an extended configuration. The pull tab 314 enables the sheath to be extended without contacting it. The pull tab may also be used to compress the sheath, if there is a need to remove the interface cable during the procedure. The pull tab can be made from a plastic such as ABS to give it the mechanical rigidity needed to manipulate the sleeve.

As shown in FIG. 16A, the sterile sheath 302 is folded (e.g. concertina folded) in a compressed position. The sterile sheath 302 may have a length of 1.5 metres or more so that its second end is outside of the sterile zone when extended. The sheath may be made from a translucent material allowing the user to see the cable that it surrounds. For example, the sheath can be made out of low density polyethylene (LDPE) or a similar material providing the flexibility and robustness required of a thin sheet material. Ideally the sleeve will be as thin as possible, e.g. 0.25 mm. The sleeve may be coloured, e.g. blue, to allow users to see immediately that the sheath is in place and intact.

The pull tab 314 or the second end 312 of the sheath may be secured to the generator to completely enclose the interface cable. In one embodiment, the sheath may include a resiliently deformable (e.g. elastic) section that is stretchable to reach the generator, whereby the sheath is naturally held taut at the generator and thereby forms a smooth cylindrical barrier.

The materials of the sheath, adhesive and cover may be selected to enable the sheath to be sterilised in a number of ways. For example, the materials proposed above are compatible with both ethylene oxide (EtO) and gamma irradiation sterilisation methods. As a result the sleeve does not reduce the options for sterilisation methods most preferred for single use instruments and allows product development teams the opportunity to select the optimal method of sterilisation for the product, rather than be driven by the sleeve itself.

In use, the sterile sheath is initially presented as a compressed sleeve (as shown in FIG. 16A) with an exposed tab protruding so that it is clearly visible to a user setting up the instrument. Preferably, an inner surface of the sheath is exposed on the outside of the device. This is so that there is no risk of contact with the area of the instrument intended to be sterile. This setup allows the instrument to be presented by a clean nurse or surgeon to a circulating nurse to connect the interface cable to the instrument connector easily without a risk to the sterility of the device. Once the cable is connected the circulating nurse is required to grasp and withdraw the tab along the length of the cable. This extends the sleeve allowing a sterile barrier to be produced over the non-sterile cable.

If the instrument in use needs to be exchanged for another instrument there are two options, firstly to use a different interface cable and to connect the second instrument in the same manner as the first, or to swap instruments on the first interface cable.

In order to swap instruments the tab used to extend the sleeve has to be used to withdraw the sleeve from the interface cable. This will cause the outer or exposed surface to fold back on itself exposing the inner, non-sterile surface which can be handled. This can then be compressed so that the interface cable can be reached and detached from the instrument. Allowing the interface cable to be swapped to the second instrument, and the first to be discarded.

FIG. 16B shows another example of an extendable sterile sheath 302. Features in common with FIG. 16A are given the same reference number and are not described again. In this embodiment, the sterile sheath 302 is part of a separate accessory that can be detachably mounted, e.g. by way of push fit, on to the handle 304. For example, in this embodiment the connection port 306 is disposed on a distal end of a protruding neck 316 which extends away from the handle 304. The protruding neck 316 has a radially extending flange 318, which acts to retain a collar 320 to which the first end 303 of the sterile sheath 302 is secured (via adhesive 308). Thus, in this embodiment, instead of the sleeve and retention component being bonded onto the rear face of the instrument handle, it is provided as a separate (detachable) piece. This accessory may be supplied with the device for the surgeon to select whether to use or not. This would mean that a sterile cap containing the sleeve could be included in the instrument packaging as a separate component.

Figure 17:
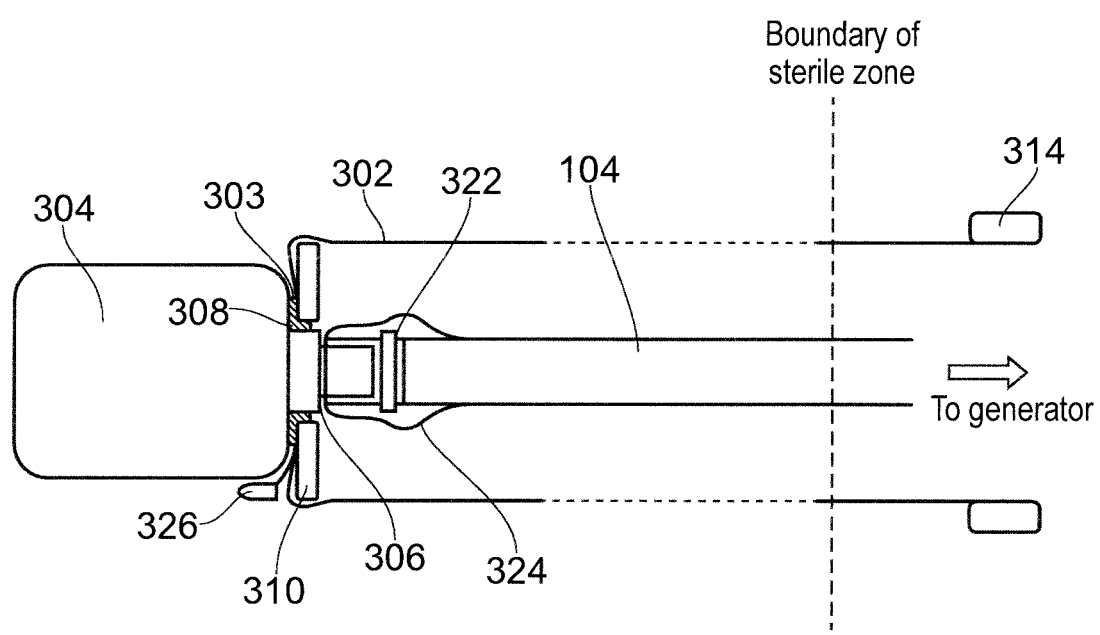
FIG. 17 is a schematic cross-sectional view of an extendable and retractable sterile sheath that is an embodiment of an invention in a extended configuration in which it provides a sterile cover for an interface cable.

FIG. 17 shows an example of an extendable sterile sheath 302 in an extended configuration. Features in common with FIGS. 16A and 16B are given the same reference number and are not described again.

In this embodiment, a cable 104 is shown connected to the connector port 306 via a suitable mating terminal connector 322 (e.g. a QMA connector). An overmoulded housing 324 as discussed above may be formed on the terminal connector 322. In this embodiment, a draw string (not shown) is attached to the sheath 302. When the pull tab 314 is pulled to extend the sheath, the draw string follows the sheath and adopts an extended position. A distal end of the draw string may pass through a hole formed in the annular cover 310. A distal end of the draw string may have a toggle 326 attached to it that is bigger than the hole to prevent the draw string from being pulled away from the cover 310. The toggle 326 is accessible on the outside of the sheath 302 and can be pulled from within the sterile field allowing the sleeve to be compressed without contact with the non-sterile tab or the sleeve. This would enable exchange of devices without any member of the operating staff contacting the sleeve and would reduce the risk of cross-contamination of the sterile field.

The invention claimed is:

1. An electrosurgical apparatus comprising:
    an electrosurgical instrument for delivering RF energy or microwave frequency energy into biological tissue; and
    an interface cable for conveying radiofrequency (RF) or microwave frequency energy between an electrosurgical generator and the electrosurgical instrument,
    wherein there is an electrical connection between the interface cable and the electrosurgical instrument;
    wherein the electrosurgical instrument comprises:

a connection interface that is cooperable with a terminal connector of the interface cable, and a sterile barrier sheath surrounding the connection interface, the sterile barrier sheath being extendable over a portion of the interface cable to surround a connection between the connection interface and the terminal connector; and wherein the electrosurgical apparatus further includes an electrically insulating tubular body secured around a circumference of the terminal connector of the interface cable, the electrically insulating tubular body having a passage therethrough which is open at a first end to expose an end of the terminal connector and through which the interface cable extends.

2. The electrosurgical apparatus according to claim 1, wherein the sterile barrier sheath has a first end secured to the electrosurgical instrument.

3. The electrosurgical apparatus according to claim 2, wherein the first end of the sterile barrier sheath is secured to a collar that is detachably mounted on the electrosurgical instrument.

4. The electrosurgical apparatus according to claim 1, wherein the sterile barrier sheath is movable from a compressed configuration, in which it defines an access opening for the connection interface, to an extended configuration, in which it extends to cover a length of the interface cable.

5. The electrosurgical apparatus according to claim 4, wherein the sterile barrier sheath comprises a length of tubing that is concertina folded when in the compressed configuration.

6. The electrosurgical apparatus according to claim 4, wherein the sterile barrier sheath has a first end secured to the electrosurgical instrument and a second end opposite to the first end, whereby the second end is movable relative to the first end to transfer the sterile barrier sheath between the compressed configuration and the extended configuration.

7. The electrosurgical apparatus according to claim 6, wherein the second end has a grippable pull tab attached thereto.

8. The electrosurgical apparatus according to claim 6, wherein the second end is securable to the electrosurgical generator.

9. The electrosurgical apparatus according to claim 1, wherein the electrosurgical instrument and sterile barrier sheath are sterilisable.

10. The electrosurgical apparatus according to claim 1, wherein the electrically insulating tubular body is overmoulded on the terminal connector.

11. The electrosurgical apparatus according to claim 1, wherein the electrically insulating tubular body has an inwardly projecting rib in the passage, the inwardly projecting rib being arranged to abut the terminal connector to seal the passage.

12. The electrosurgical apparatus according to claim 1, wherein the electrically insulating tubular body is made of biocompatible material.

13. The electrosurgical apparatus according to claim 1, wherein the interface cable comprises:

a coaxial cable for conveying the RF or microwave frequency energy;

a proximal connector at a first end of the coaxial cable, the proximal connector being arranged to form an electrical connection with a cooperating connection interface on the electrosurgical generator; and an insulating housing mounted over the proximal connector, the insulating housing comprising a proximal tubular body secured around the circumference of the proximal connector, wherein the terminal connector is at a second end of the coaxial cable.

14. The electrosurgical apparatus according to claim 13, wherein the proximal tubular body is overmoulded on the proximal connector.

15. The electrosurgical apparatus according to claim 1, wherein the sterile barrier sheath is extendable to the proximal connector at the first end of the coaxial cable.

* * * * *

UNITED STATES PATENT AND TRADEMARK OFFICE
CERTIFICATE OF CORRECTION

| | | |
|---|---|---|
| PATENT NO. | : 10,610,284 B2 | Page 1 of 1 |
| APPLICATION NO. | : 15/327569 | |
| DATED | : April 7, 2020 | |
| INVENTOR(S) | : Christopher Paul Hancock | |

It is certified that error appears in the above-identified patent and that said Letters Patent is hereby corrected as shown below:

On the Title Page

(73) Assignee Reads:
CREA MEDICAL LIMITED

Should Read:
CREO MEDICAL LIMITED

Signed and Sealed this
Twelfth Day of May, 2020

Andrei Iancu
*Director of the United States Patent and Trademark Office*